United States Patent
Edelen et al.

(10) Patent No.: US 9,533,302 B2
(45) Date of Patent: Jan. 3, 2017

(54) FLUID CARTRIDGE AND SYSTEM FOR DISPENSING FLUID

(75) Inventors: John Glenn Edelen, Versailles, KY (US); James Daniel Anderson, Jr., Harrodsburg, KY (US); Steven W. Bergstedt, Winchester, KY (US); Yimin Guan, Lexington, KY (US)

(73) Assignee: Lexmark International, Inc., Lexington, KY (US)

( * ) Notice: Subject to any disclaimer, the term of this patent is extended or adjusted under 35 U.S.C. 154(b) by 0 days.

(21) Appl. No.: 13/416,485

(22) Filed: Mar. 9, 2012

(65) Prior Publication Data
US 2013/0236374 A1  Sep. 12, 2013

(51) Int. Cl.
| | |
|---|---|
| C12M 1/34 | (2006.01) |
| B01L 3/00 | (2006.01) |
| A61J 3/00 | (2006.01) |
| B01L 3/02 | (2006.01) |
| G01N 1/00 | (2006.01) |
| B41J 29/00 | (2006.01) |
| B41J 29/38 | (2006.01) |
| C12M 1/36 | (2006.01) |

(52) U.S. Cl.
CPC ............ *B01L 3/0293* (2013.01); *B01L 3/0268* (2013.01); *B01L 2200/028* (2013.01); *B01L 2200/061* (2013.01); *B01L 2200/0642* (2013.01); *B01L 2200/143* (2013.01); *B01L 2200/147* (2013.01); *B01L 2400/02* (2013.01); *B01L 2400/0439* (2013.01); *B01L 2400/0442* (2013.01); *C12M 41/48* (2013.01)

(58) Field of Classification Search
CPC .................. B01L 2200/028; B01L 2200/147; B01L 2400/0439; B01L 2400/0442; B01L 3/0268; B01L 3/0293; B01L 2200/0642; B01L 2200/061; B01L 2200/143; B01L 2400/02; C12M 41/48
USPC .......................................... 422/68.1, 502–560
See application file for complete search history.

(56) References Cited

U.S. PATENT DOCUMENTS

| | | | |
|---|---|---|---|
| 6,682,899 B2 * | 1/2004 | Bryan et al. .................. 435/7.1 |
| 6,749,288 B2 | 6/2004 | Ahne | |
| 7,083,266 B2 | 8/2006 | Ahne | |
| 7,201,732 B2 * | 4/2007 | Anderson et al. .............. 604/66 |

(Continued)

OTHER PUBLICATIONS

Jeff Nielsen, Michael Day, Christie Dudenhoefer, Heather Paris, Kevin F. Peters, Debora Thomas, Ken Ward and Joshua Yu; Hewlett-Packard Company, Corvallis, Oregon, USA; Thermal Inkjet System to Enable Picoliter Dispense of Pharmaceutical Compounds, pp. 172-175; NIP 27 and Digital Fabrication 2011 Technical Program and Proceedings; 2011 Society for Imaging Science and Technology.

*Primary Examiner* — Jennifer Wecker

(57) ABSTRACT

A fluid cartridge has a bottle to retain a volume of fluid. An ejector chip resides in fluid communication with the bottle and causes ejection of fluid upon activation of fluid ejectors. Control logic coordinates ejector activation with dose control logic and temperature control circuitry. The dose control logic pre-specifies an amount of fluid to be ejected and prevents further ejection upon reaching the amount. Meanwhile, the temperature control circuit inhibits any ejection until a temperature of the fluid is within a predefined acceptable range. Bottle modularity, fluid dispense-areas and group-control of the ejectors facilitate certain designs.

18 Claims, 12 Drawing Sheets

(56) References Cited

U.S. PATENT DOCUMENTS

| | | | |
|---|---|---|---|
| 7,384,115 B2* | 6/2008 | Barkley | 347/17 |
| 7,589,552 B1* | 9/2009 | Guzman | H03K 19/0075 326/10 |
| 7,909,424 B2 | 3/2011 | Giri | |
| 2002/0080658 A1* | 6/2002 | Signorelli | G06F 11/006 365/200 |
| 2002/0159919 A1* | 10/2002 | Churchill | B01J 19/0046 422/400 |
| 2003/0032198 A1* | 2/2003 | Lugmair et al. | 436/180 |
| 2004/0085399 A1* | 5/2004 | Ahne et al. | 347/50 |
| 2005/0101019 A1* | 5/2005 | McClelland et al. | 435/459 |
| 2005/0129746 A1* | 6/2005 | Lee et al. | 424/443 |
| 2007/0040859 A1* | 2/2007 | Kimura | 347/7 |
| 2009/0097084 A1* | 4/2009 | Bergstedt et al. | 358/530 |
| 2009/0160898 A1* | 6/2009 | Bergstedt et al. | 347/17 |
| 2010/0261661 A1 | 10/2010 | Astrup | |
| 2012/0051984 A1* | 3/2012 | Dudenhoefer et al. | 422/502 |
| 2013/0078733 A1* | 3/2013 | Holmes et al. | 436/174 |
| 2013/0217106 A1* | 8/2013 | Jones | 435/287.2 |

\* cited by examiner

FLUID CARTRIDGE AND SYSTEM FOR DISPENSING FLUID

FIELD OF THE DISCLOSURE

The present disclosure relates to dispensing fluid or liquid. It relates particularly to a cartridge and control for dispensing varieties of liquid with precision.

BACKGROUND

The ability to accurately dispense liquids has broad applications in the laboratory automation and healthcare fields. Within the field of Point-of-Care (POC) diagnostics it is anticipated that applications will exist where it is desirable to deliver a precise amount of liquid to a predefined area. It is further anticipated that these applications will necessitate control devices where small size and portability will be highly valued.

There presently exist many methods for delivering fluids within the laboratory and POC fields. These include mechanical methods such as metered dose inhalers (MDI), peristaltic and piezo pumps and manual pipettes. These methods often have limited precision or would require a large area to incorporate within a portable device. It is therefore desirable to develop a new system to enable the next generation of POC devices.

Advantageous traits of such a system are small size, flexible volumes and high precision. Since the controllers which will incorporate these devices may have limited electrical input and output capabilities it is also desired to enable a simplified control interface. A further requirement is the ability to dispense a range of liquids while limiting any undesirable chemical interactions within the device.

A novel fluid delivery system meeting these needs is fully described is this disclosure.

DETAILED DESCRIPTION OF THE ILLUSTRATED EMBODIMENTS

Each component of the system will be described in sufficient detail to allow those skilled in the art to practice the invention.

Figure 1:
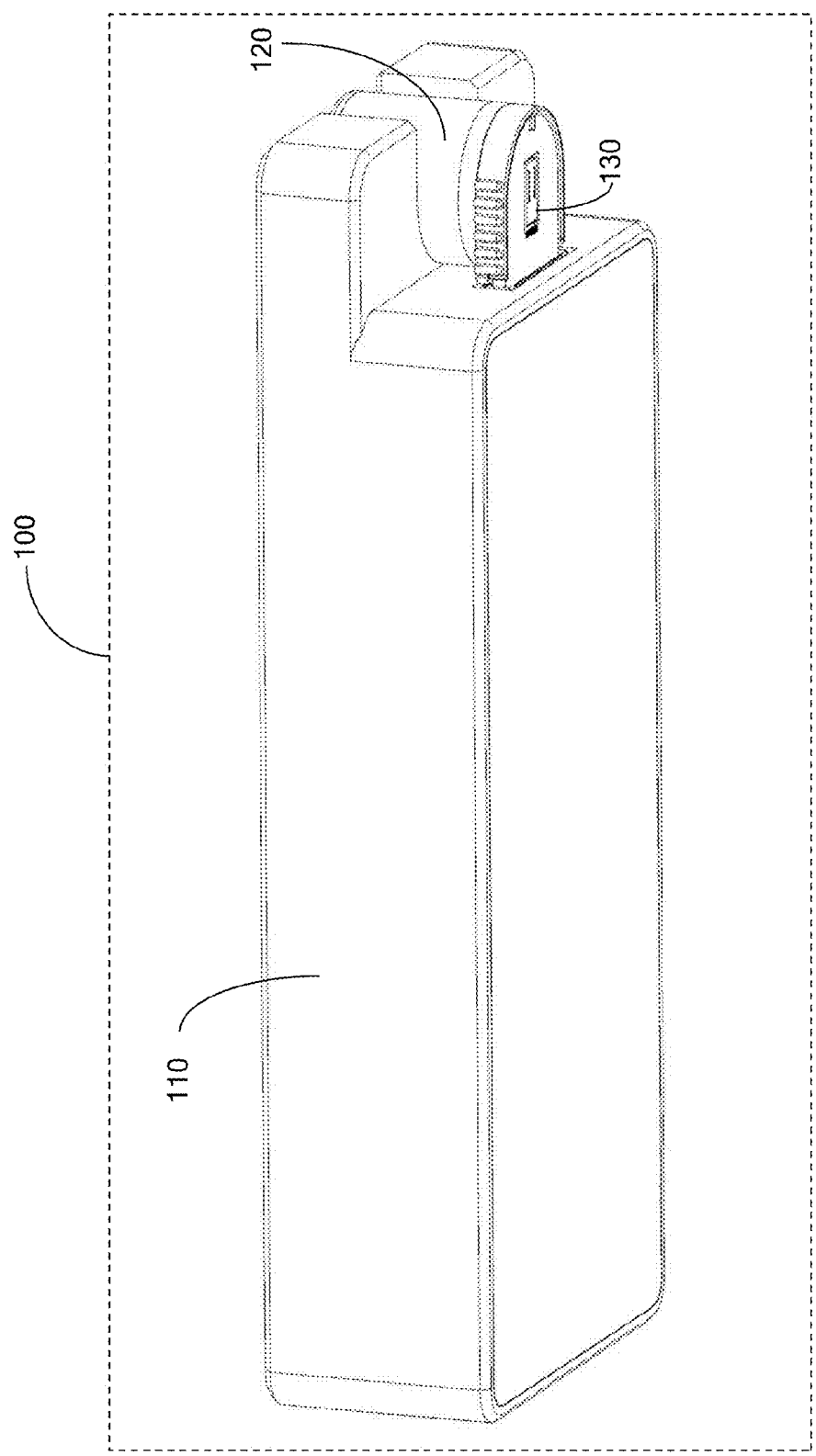
FIG. 1 illustrates a perspective view of an exemplary embodiment of a system for dispensing liquid.

FIG. 1 shows an embodiment of the fluid delivery system 100. The fluid delivery system consists of a control device 110 which is designed to accept a fluid cartridge 120. A programmable ejector chip 130 is incorporated into the fluid cartridge to dispense liquid. Each component of the system will now be fully described.

Ejector chip 130 uses thermally actuated ejectors as is common in micro-fluidic applications, such as inkjet printing. The primary difference between the disclosed ejector chip and those normally used in printing applications is the addition of control logic designed to simplify the electrical interface to the ejector chip. This simplified control logic (200, FIG. 2) is incorporated into the ejector chip 130. While the exemplary embodiment uses thermally actuated ejectors it should be understood that other types of ejectors, for example piezoelectric, could be used as well.

Figure 2:
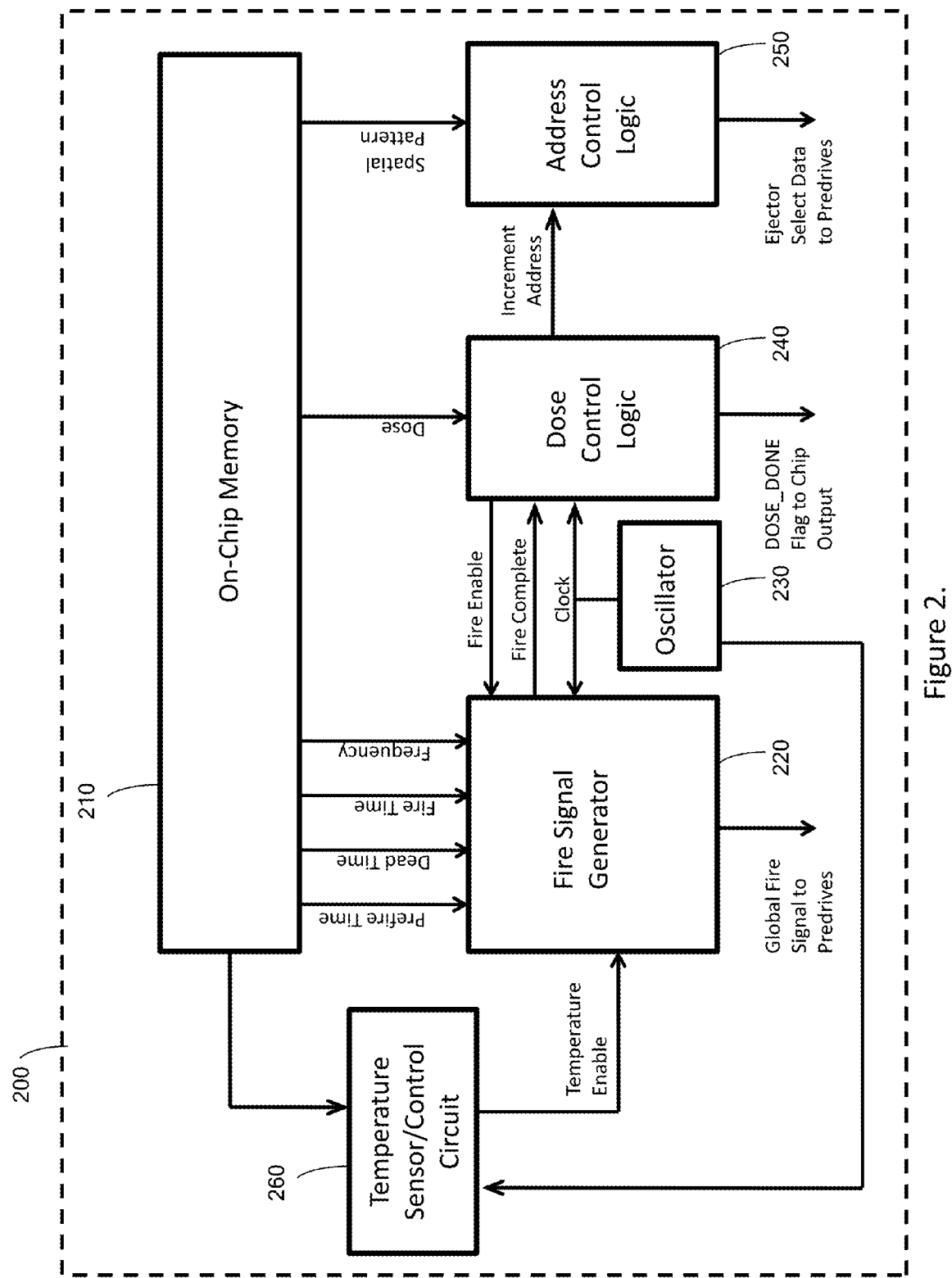
FIG. 2 is a block diagram of the ejector chip control logic according to an embodiment of the invention.

A simplified block diagram of the control logic 200 is shown in FIG. 2. In this embodiment 64 bits of On-Chip Memory 210 is provided to store the parameters necessary to deliver the desired dose. In this embodiment the memory is made up of polysilicon fuses. It will be recognized by those skilled in the art that other memory technologies could just as easily be used. These memory types include floating gate, EPROM, EEPROM, DRAM etc. For this application fuse technology is used to simplify the required support logic.

It is the use of the On-Chip Memory 210 which enables a simplified interface between the fluid cartridge 120 and the control device 110. The On-Chip Memory is used to store an energy pulse profile, an amount of liquid to dispense, a spatial pattern of ejectors and a desired temperature of the liquid when it is to be ejected. With these parameters pre-defined, the electrical interface can be simplified to four inputs: 1) power to drive ejectors; 2) power to drive chip logic circuits; 3) a logic enable signal; and 4) a common electrical ground connection. In cases where the ejectors and logic circuits share a common voltage, the interface can be reduced to three inputs: 1) power, 2) a logic enable signal and 3) electrical ground. If the application does not require or cannot support an enable signal, the interface can be further reduced to power and electrical ground only where the enable signal is tied to the common power.

As shown in FIG. 2 the On-Chip Memory 210 is coupled to a Fire Signal Generator 220. The Fire Signal Generator will output to the thermal ejectors (Global Fire Signal) an energy pulse based on the pre-programmed memory. When using thermal actuators to eject a drop of liquid, it is known that the energy pulse timing is critical to optimize the jetting performance. The energy pulse can be broken into 3 segments; the pre-fire time, dead time, and main fire time. These parameters are passed from the On-Chip Memory to the Fire Signal Generator. The pre-fire is optional in some applications but is often used to supply an initial amount of energy (less than that necessary for ejection) to the liquid. This provides higher velocity ejection of liquid drops. The dead time is defined as the amount of time between the pre-fire and main fire time. This time is used to allow for the thermal energy from the pre-fire pulse to transfer to the liquid. The main fire time is the duration of the energy pulse which nucleates the liquid causing drop ejection.

The Fire Signal Generator 220 is further coupled to an on-chip Oscillator 230. For this application the Oscillator is designed to provide a nominal 10 MHz Clock signal. The energy pulse is generated by counting Clock cycles generated by the Oscillator. As also shown in FIG. 2, the Fire Signal Generator receives a memory input related to the ejector frequency. This allows the Fire Signal Generator to pause for the pre-programmed number of clock cycles. This limits the frequency at which a single ejector will be energized which is necessary to allow for proper ejection chamber refill times.

Referring again to FIG. 2, the Dose Control Logic 240 is coupled to the On-Chip Memory 210 as well as the Oscillator 230. The Dose Control Logic will enable the Fire Signal Generator 220 to create the ejector energy pulse a pre-programmed number of times. This is accomplished by counting the number of ejector energy pulses completed. In this way the ejector chip 130 can be configured to deliver a controlled amount of liquid. For example, in an application where a precise 5 uL of liquid is required, the number of energy pulses necessary for that particular ejector chip can be stored in memory. As illustrated in FIG. 2, the Dose Control Logic will also set the output DOSE_DONE to a logic high state when the desired number of fires has been reached. This can be used to provide feedback to the control device 110.

The Address Control Logic 250 generates the ejector address information based on a desired spatial pattern of ejectors. The overall ejector addressing is based on the number of ejector groups (G) and the number of ejectors per group (H). The G×H addressing will be explained in greater detail in the discussion of FIG. 5. In this embodiment there are 16 ejector groups (G=16) and 16 ejectors per group (H=16) so that the total number of ejectors is G×H=256. After each ejector energy pulse is completed the Dose Control Logic 240 will increment the address count within the Address Control Logic. The Address Control Logic will complete the G×H address matrix by selecting only those ejector groups pre-defined in the On-Chip Memory. This allows the user to select the ejection pattern based on any combination of the 16 ejector groups. This provides significant flexibility in defining the dispense area.

Referring again to FIG. 2, the Temperature Sensor/Control Circuit 260 is coupled to On-Chip Memory 210, Fire Signal Generator 220 and Oscillator 230. It is known that thermal drop ejection is highly dependent on the liquid viscosity which in turn is directly related to the liquid temperature. To achieve reliable and well controlled thermal ejection the ability to accurately control the ejector chip temperature is a necessity. For example, an ejector designed to deliver 24 pL of fluid at 45 degrees Celsius will actually deliver about 17 pL at 22 degrees Celsius. Thus, the Temperature Sensor/Control Circuit allows the user of ejector chip 130 to program in the desired temperature as a binary value so that accurate control of the temperature is obtained and a precise amount of fluid is ejected. At chip power up, the Temperature Sensor/Control Circuit will gate the Fire Signal Generator so that no ejectors can be addressed until the chip temperature is within a preset range of the programmed value. In this embodiment the system is designed to begin drop ejection when within 3 degrees Celsius of the programmed value. Of course, control could be limited to prevent ejection within other temperature degrees of operation.

Figure 3:
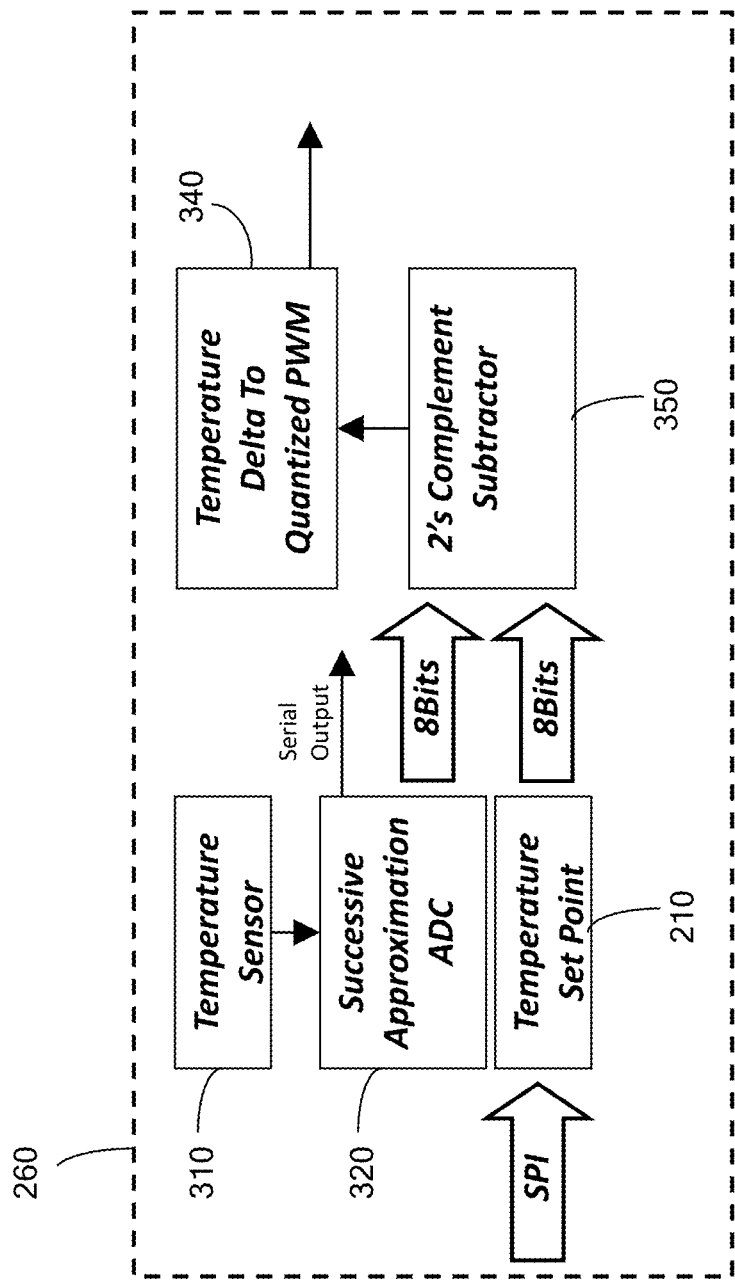
FIG. 3 is a block diagram of the ejector chip thermal control system according to an embodiment of the invention.

A block diagram of the Temperature Sensor/Control Circuit 260 is shown in FIG. 3. In this embodiment the Temperature Sensor 310 is made up of bi-polar devices in the ejection chip configured to generate an output current which is proportional to absolute temperature. The Temperature Sensor output current increases linearly with temperature. Its current output is converted to an 8 bit count by a Successive Approximation Analog to Digital Converter (ADC) 320. The ADC uses the Oscillator 230 as a clock source and from it develops a conversion clock with a nominal frequency of 39.2 kHz. The ADC is accomplished by comparison of the Temperature Sensor current to a fixed temperature independent reference current. For example, at 30 degrees Celsius the Temperature Sensor current will be about 20 uA while the reference current will be about 5 uA. In this case a constant 15 uA independent reference current is subtracted from the Temperature Sensor current during ADC conversion. If the Temperature Sensor current is greater than the reference current then the reference current is subtracted from the Temperature Sensor output current and the most significant bit (MSB) of the ADC count is set to logic 1. If the Temperature Sensor current is less than the reference current then the MSB is set to logic 0. The reference current is then reduced by ½ and the comparison is repeated 7 times until all bits of the ADC 8 bit count are defined. The ADC is output serially with a logic 1 start bit then starting from the LSB to the MSB the ADC count is transmitted to the serial output pin. The conversion time for the entire 8 bit ADC count is 10 of its 39.2 kHz clocks or 255 micro seconds.

The 8 bit ADC count is output to a 2's Complement Subtractor 350. A Temperature Set Point stored in the On-Chip Memory 210 is also output to the 2's Complement Subtractor. The output of the 2's Complement Subtractor determines the heat pulse output of the Temperature Delta To Quantized PWM 340. If the difference between the Temperature Set Point and the ADC count (or Temperature Delta) is greater than 3 counts then 100% PWM (maximum heating) is applied. If the Temperature Delta is 3 counts or less then a heat pulse duty cycle is reduced from 100% down to 0% quantized in 25% increments. The heat pulse is terminated when the Temperature Delta is 0 counts. This method optimizes system stability by modulating the thermal energy applied to the ejector chip 130. The system uses an inverse relationship between applied thermal energy and target temperature delta to minimize system overshoot.

Temperature Sensor/Control Circuit 260 will enable the Fire Signal Generator 220 by setting the Temperature Enable signal to logic 1 state when the Temperature Delta is less than 3 counts. Using the thermal control system as described the startup sequence for ejector chip 130 will bring the ejector chip to the pre-programmed temperature and begin dispensing only when the temperature is within 3 degrees of the set point.

The 8 bit ADC count may be read as a serial output during wafer level testing. Here the chip temperature may be set by a thermal chuck used to force the chip to the Temperature Set Point at wafer probe. For example if it is desired to dispense fluid at 45 degrees Celsius the output of the ADC can be read during a wafer level test while being held at 45 degrees Celsius. This value can then be stored in the On Chip Memory 210. When power is now applied to ejector chip 130 the Temperature Sensor/Control Circuit 260 will attempt to heat the ejector chip until the output of the ADC reaches the stored value. In this manner the ADC need not have high accuracy over its full range as it only needs to be accurate over a narrow range near the particular Temperature Set Point.

Figure 4:
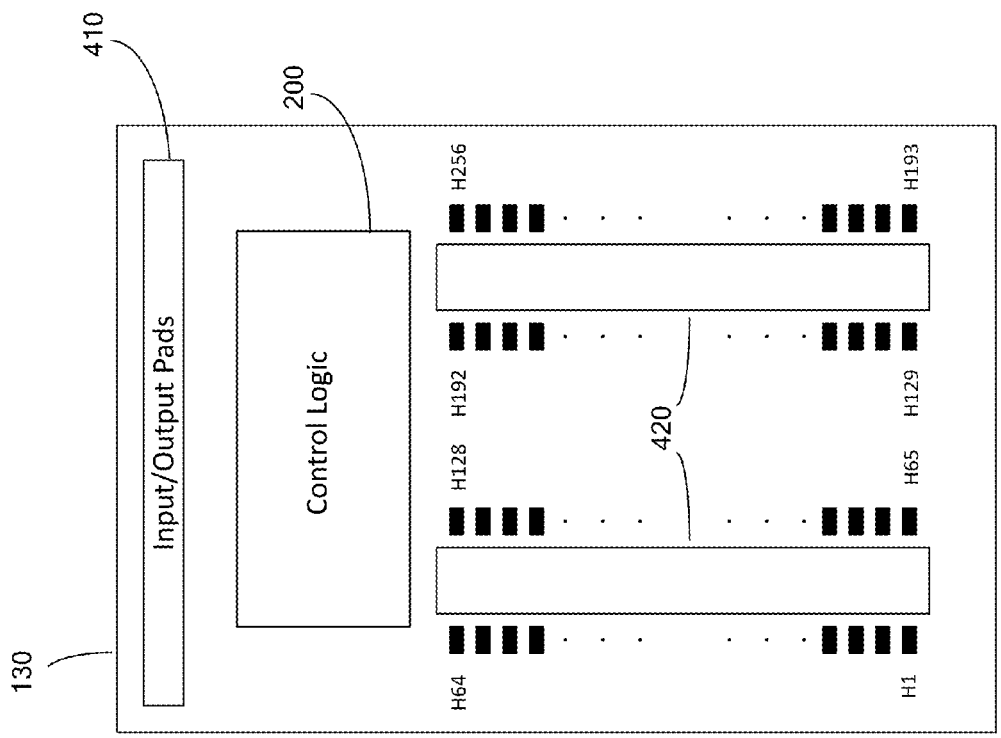
FIG. 4 illustrates an ejector chip floor plan according to an embodiment of the invention.

FIG. 4 shows a preferred embodiment of the ejector chip 130 floor map where the Control Logic 200 is restricted to one end of the ejector chip. This allows the Control Logic block to be used in a modular manner. In this way the number, location and type of ejectors can be modified without significant change to the Control Logic block. The Control Logic is also located in close proximity to the ejector chip Input/Output Pads 410. By co-locating the Control Logic and Input/Output Pads the routing of the interconnect traces can be simplified. This allows the designer to minimize the number of metal layers needed which in turn will reduce ejector chip cost. In this embodiment there are two thru chip vias 420 which allow liquid to pass from the fluid cartridge 120 to the thermal ejectors shown as H1 through H256. In this embodiment the ejector chip substrate is made from single crystal silicon. The vias are formed with a dry etch process such as DRIE but could also be formed by other means such as chemical etching or grit blasting.

Figure 5:
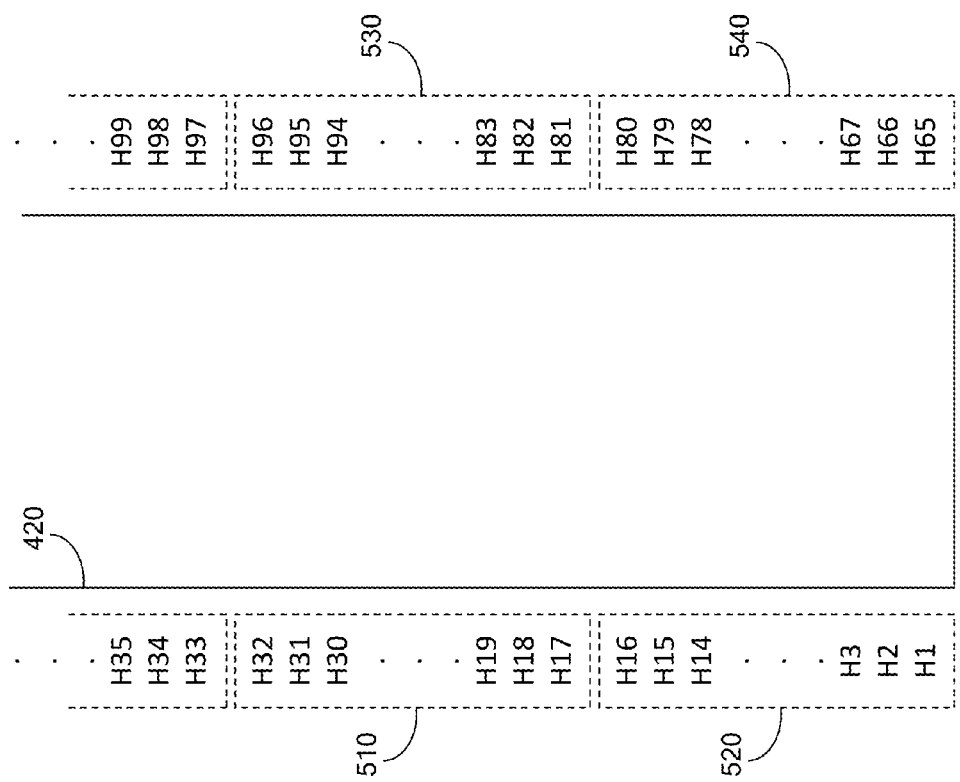
FIG. 5 illustrates an ejector addressing architecture according to an embodiment of the invention.

As previously discussed, the ejector address matrix consists of H ejectors by G ejector groups. FIG. 5 represents the H×G ejectors addressing for the bottom portion of one via 420. As seen, the via is shown with four ejector groups; H1 520, H2 510, H5 540 and H6 530. In turn, each ejector group is made up of 16 ejectors. By use of the On-Chip Memory 210 coupled with the Address Control Logic 250 the desired dispense area can be selected. It will be apparent to those skilled in the art that while the preferred embodiment shows ejectors located adjacent to two continuous vias other ejector and via configurations could be realized. For example if the desired dispense area is a square the 256 ejectors could be arranged as an evenly spaced 16×16 matrix with individual vias for each ejector.

In an exemplary embodiment as illustrated in FIG. 4, the maximum dispense area is defined in the vertical direction by the distance between ejectors H1 and H64 which is about 4 mm while the maximum dispense area is defined in the horizontal direction by the distance between H1 and H193 which is about 2 mm. This represents the case where the user has selected all available ejectors. In the case where the user wishes to minimize the dispense area a single set of ejectors can be selected. For example ejector group 520 as shown in FIG. 5. This would create a dispense area defined in the vertical direction by the distance between ejectors H1 and H16 which is about 9 mm. Since the user has selected a single ejector group in this example the dispense area in the horizontal direction is defined by the ejected drop size. It will be recognized by those skilled in the art that the address architecture could be modified to meet specific application needs. This could include increasing or decreasing the number of ejectors per ejector group.

The ejector chip 130 as described allows for ejector energy pulse, frequency, spatial pattern, temperature and dose to be pre-programmed into the device. This allows fluid dispensing to be easily incorporated into a broad range of applications.

This embodiment with a nominal 10 MHz oscillator can be programmed to the following values:
Pre-fire Time: 0 to 700 ns
Dead Time: 100 to 1700 ns
Fire Time: 0 to 3100 ns
Ejector Freq. Minimum of 6.6 kHz
Dose: 24 pL to 402 uL
Dispense Pattern Any combination of 16 ejector groups
Temperature: Temperature control within 3 degrees Celsius of set point In this embodiment the Pre-fire Time and Fire Time represents the actuation time for the ejector while the Dead Time represents no actuation. Using the defined times a thermal ejector would be capable of dispensing aqueous based solutions with viscosities up to about 15 cP and alcohol based solutions up to about 10 cP.

Figure 6B:
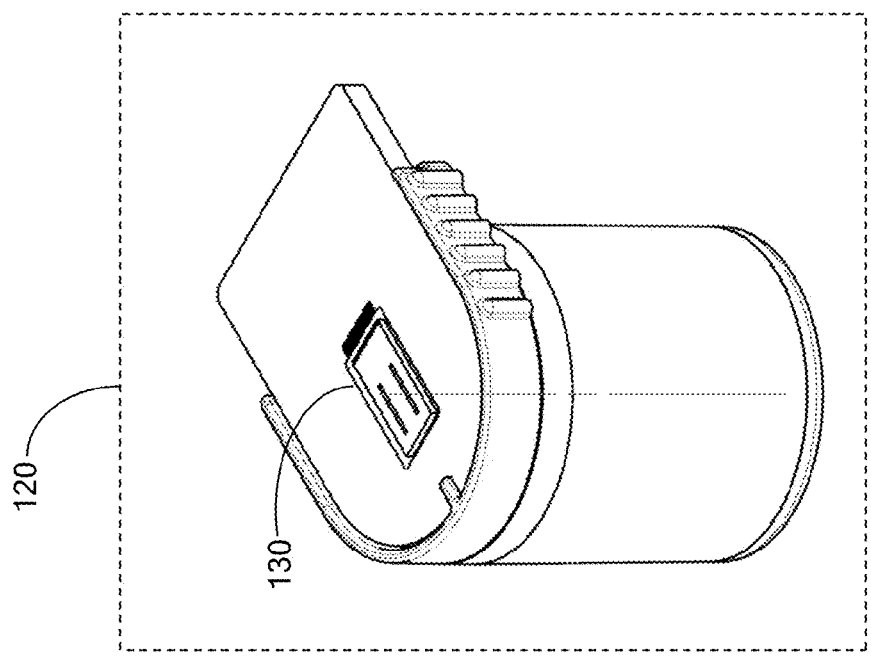
FIG. 6B illustrates a bottom perspective view of a fluid cartridge according to an embodiment of the invention.
Figure 6A:
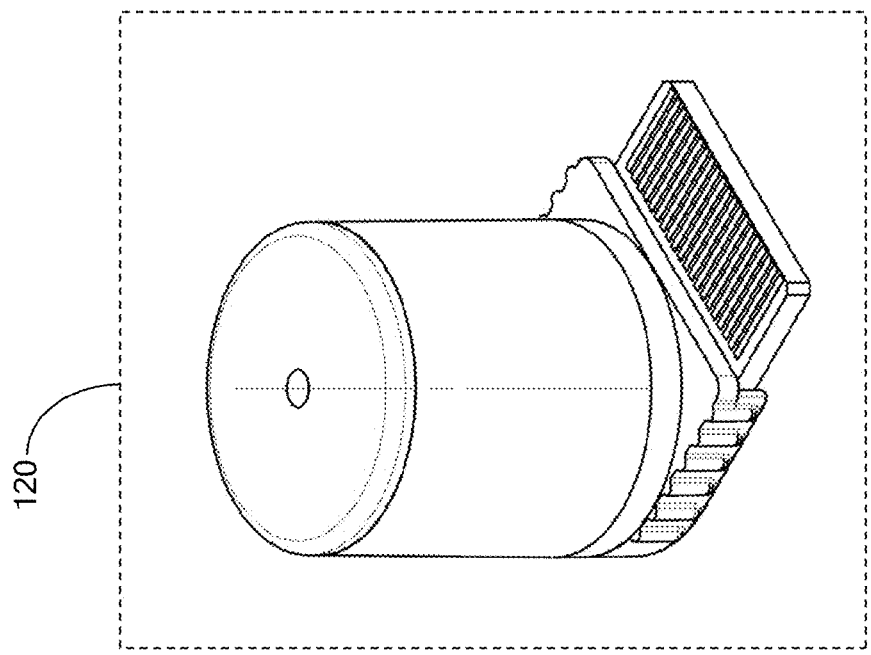
FIG. 6A illustrates a top perspective view of a fluid cartridge according to an embodiment of the invention.

FIG. 6A shows a perspective view of the fluid cartridge 120. FIG. 6B further shows the location of the ejector chip 130 attached to the bottom of the cartridge.

Figure 7:
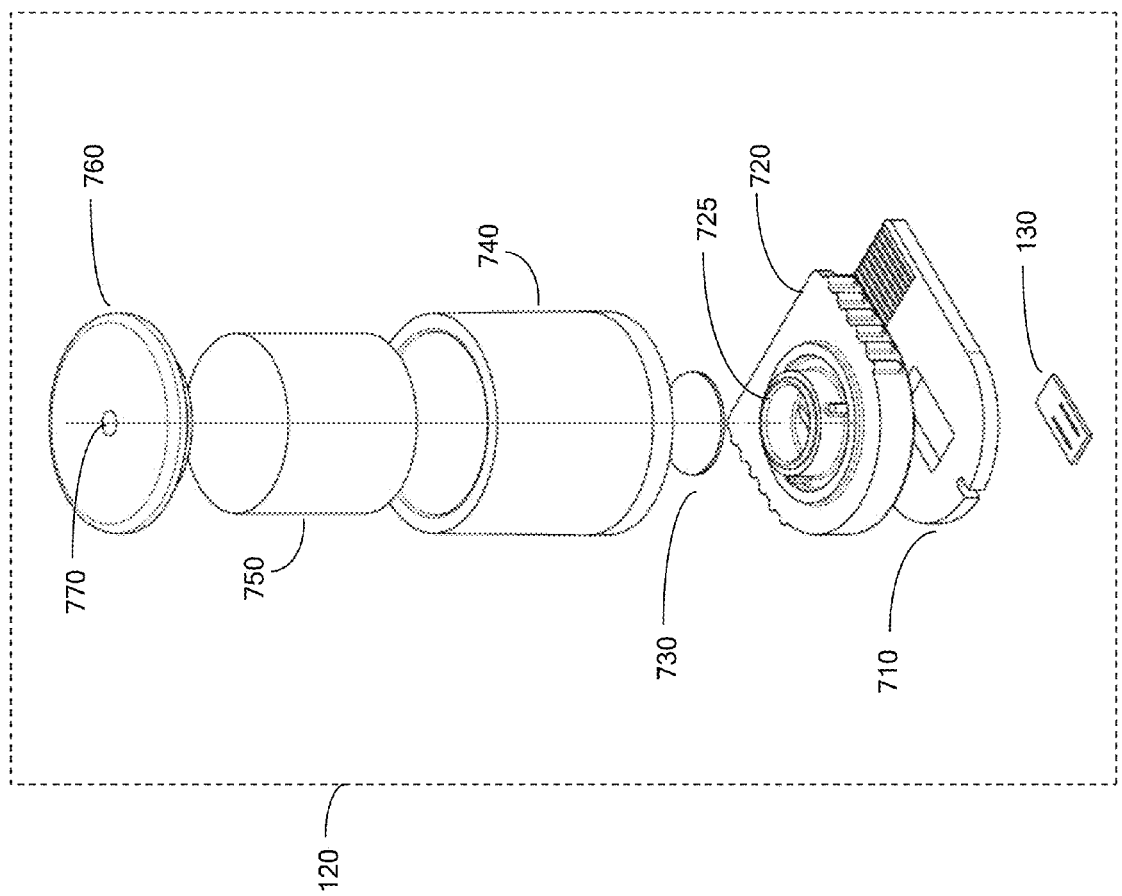
FIG. 7 illustrates an exploded view of a fluid cartridge according to an embodiment of the invention.

FIG. 7 provides an exploded view of fluid cartridge 120. During assembly the printed circuit board (PCB) 710 and ejector chip 130 are adhesively bonded to the substrate 720 with a thermal cure adhesive. The filter 730 is a random weave stainless steel filter that is heat staked to the substrate in order to create a sealed chamber below the filter. The bottle 740 is a UV transparent Noryl plastic material that is laser welded to the substrate to act as the storage volume for the fluid. The back pressure media 750 is a felt based material, that when wetted with the dispensing fluid, creates a capillary action to create a negative pressure at the nozzle plate of the ejector chip. The back pressure media is inserted into the bottle and then captured with the lid 760. The lid is a Noryl based plastic material with a carbon black colorant. The lid can be attached in a number of ways but a few are laser welding, ultrasonic welding, spin welding or adhesives. The finished fluid cartridge can be filled with liquid by syringe or other means using the fill hole 770.

Figure 8B:
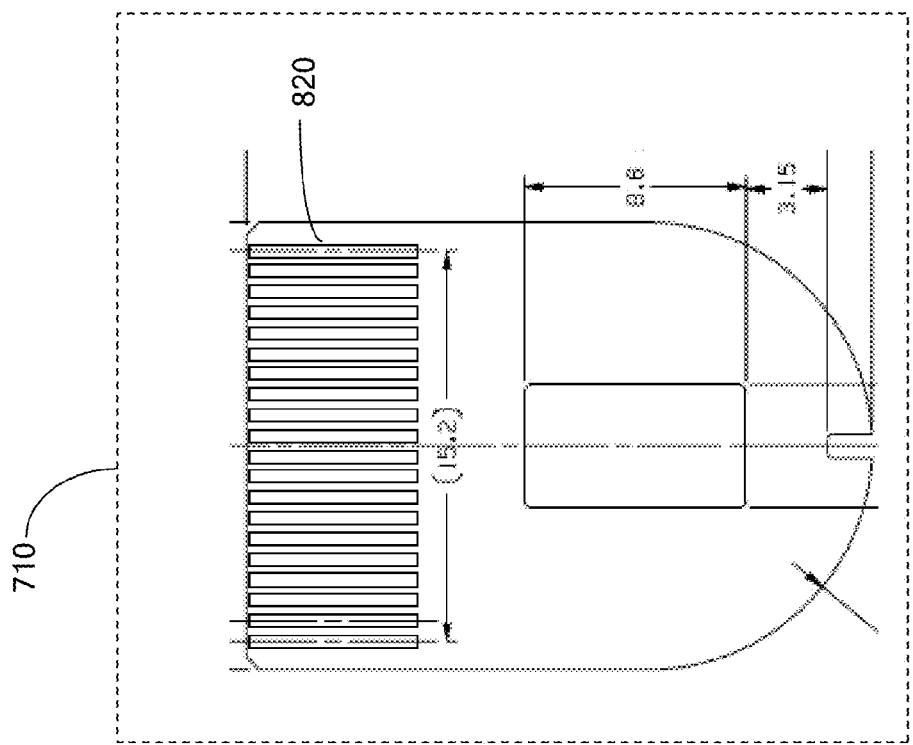
FIG. 8B illustrates the top view of a fluid cartridge printed circuit board according to an embodiment of the invention.
Figure 8A:
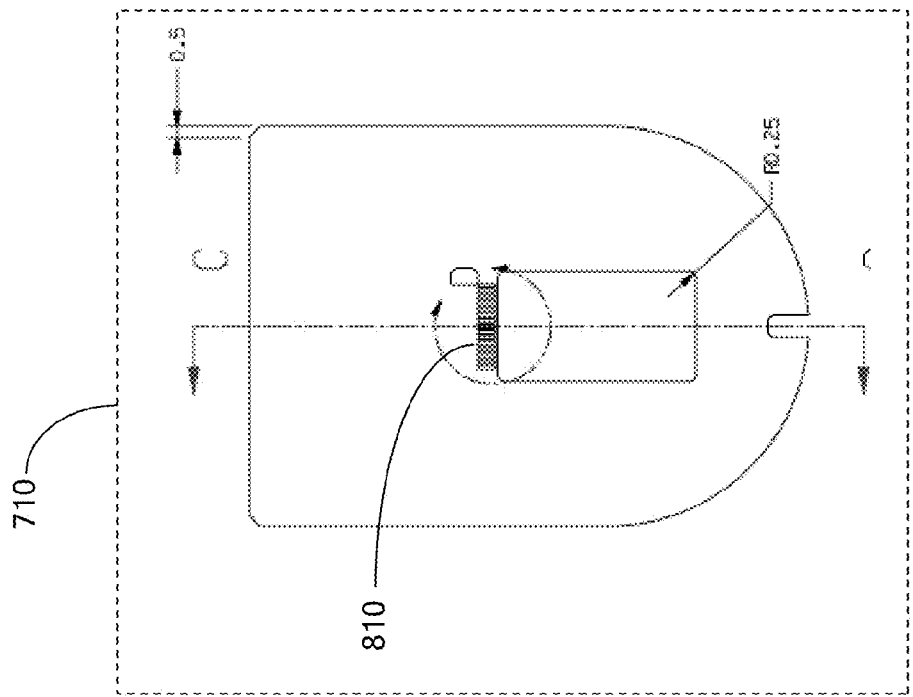
FIG. 8A illustrates the bottom view of a fluid cartridge printed circuit board according to an embodiment of the invention.

The bottom and top of the PCB 710 is shown in FIGS. 8A and 8B respectively. To maintain compatibility with the high temperature adhesive cure used for ejector chip 130 to substrate 720 bonding, a PCB material with a high glass transition temperature such as ISOLA 410 is used. The ejector chip wire bond pads 810 are soft gold to enable more consistent wire bonding between the ejector chip and PCB. To allow the fluid cartridge 120 to be quickly and easily incorporated into POC and lab automation equipment the edge card contacts 820 are arranged on a 0.8 mm pitch and the PCB thickness is chosen to be 0.063". This allows the fluid cartridge to mate with commercially available edge card connectors instead of requiring a custom electrical interconnect.

Figure 9:
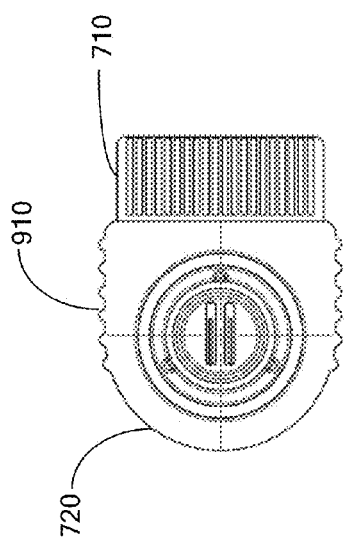
FIG. 9 illustrates the top view of the fluid cartridge substrate and printed circuit board according to an embodiment of the invention.

FIG. 9 shows design details of the PCB 710 and substrate 720 assembly. The substrate is a Noryl based plastic with no structural fill additives but does add a carbon black colorant for use with laser welding. The substrate also contains features for setting adhesive bonding height as well as ribs 910 along the sides for ease of grasping the fluid cartridge.

Figure 10:
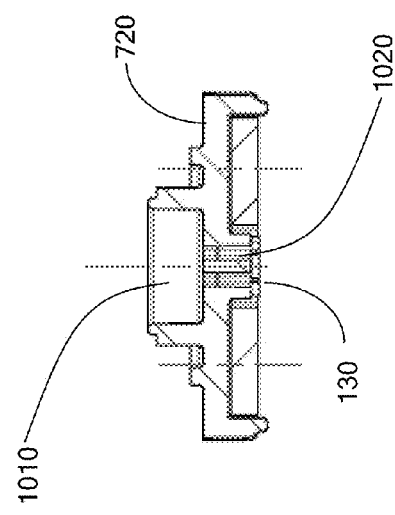
FIG. 10 illustrates a cross sectional view of the fluid cartridge substrate with fluid reservoir and flow features according to an embodiment of the invention.

In the case where the finished assembly consists of the ejector chip 130, PCB 710 and substrate 720 only, liquid can be deposited into the substrate reservoir 1010, as shown in FIG. 10, by manual pipette or automated means. This enables the use of small volumes in the order of 100 uL. As also shown in FIG. 10, flow features 1020 in the substrate allow liquid to pass through the substrate to the back side of the ejector chip.

The fluid cartridge 120 is modular in the fact that it can be put together in multiple ways. If the filter, bottle, back pressure media and lid are left off, fluid can be dispensed into the area directly above the chip for very small volumes. Likewise the bottle, lid and back pressure media can be multiple sizes and shapes as long as the UV transparent plastic of the bottle, can interface with the weld ring 725 of the printhead substrate. For example, a bottle with an inner diameter of about 12 mm and height of 10 mm will deliver about 1 mL of solution while a bottle with the same inner diameter but height of 20 mm will deliver about 2 mL. By properly adjusting the back pressure for each bottle size the fluid cartridge can be configured to deliver liquid volumes in the range of about 0.5 mL to about 5 mL. This creates a large amount of flexibility in the finished printhead, with very little tooling changes needed for specialized products.

While the back pressure media in this embodiment is a felt-based material it is understood that when working with biological samples it may be desirable to use a back pressure device which will reduce the possibility of sample contamination from the felt. Examples of such materials would be glass tubes or beads where the glass surface provides capillary force to create the necessary back pressure. Another method would be to incorporate a bladder system. A typical bladder system comprises a set of plates connected by a spring. The assembly in this case would be enclosed by a biocompatible film. As the sample material is consumed, the spring collapses and maintains a constant back pressure.

In cases where the Noryl plastics may cause sample contamination it is possible to coat the entire assembly with a $SiO_2$ layer by means of Chemical Vapor Deposition, for instance. This process allows for the uniform deposition of thin layers of material (typically 300 angstroms or less). This method can be used to encapsulate all surfaces of the fluid cartridge 120. It also allows for modifying the surface energies of the fluid cartridge depending upon application.

Figure 11:
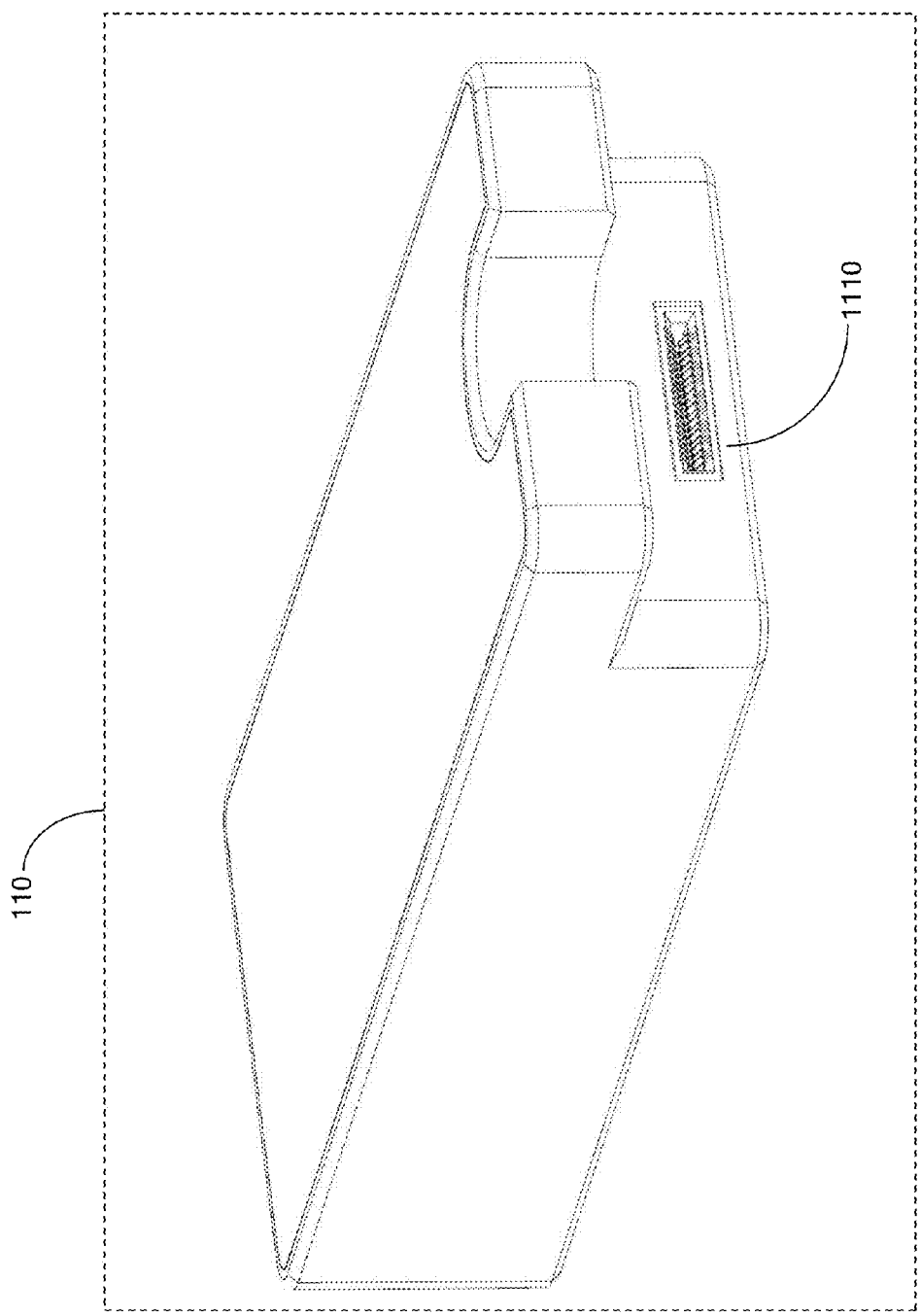
FIG. 11 illustrates a perspective view of a control device which accepts the fluid cartridge for dispensing liquid according to an embodiment of the invention.

Referring now to FIG. 11, control device 110 is shown with edge card connector 1110. In the exemplary embodiment the edge card connector is a 0.8 mm pitch connector accepting 0.063" printed circuit boards. For example Samtec part HSEC8-120-01-S-D-EM2 which mates with PCB 710 of fluid cartridge 120. As also shown in FIG. 11 the electrical enclosure for the control device is designed to provide lateral support for the fluid cartridge when inserted.

Figure 12:
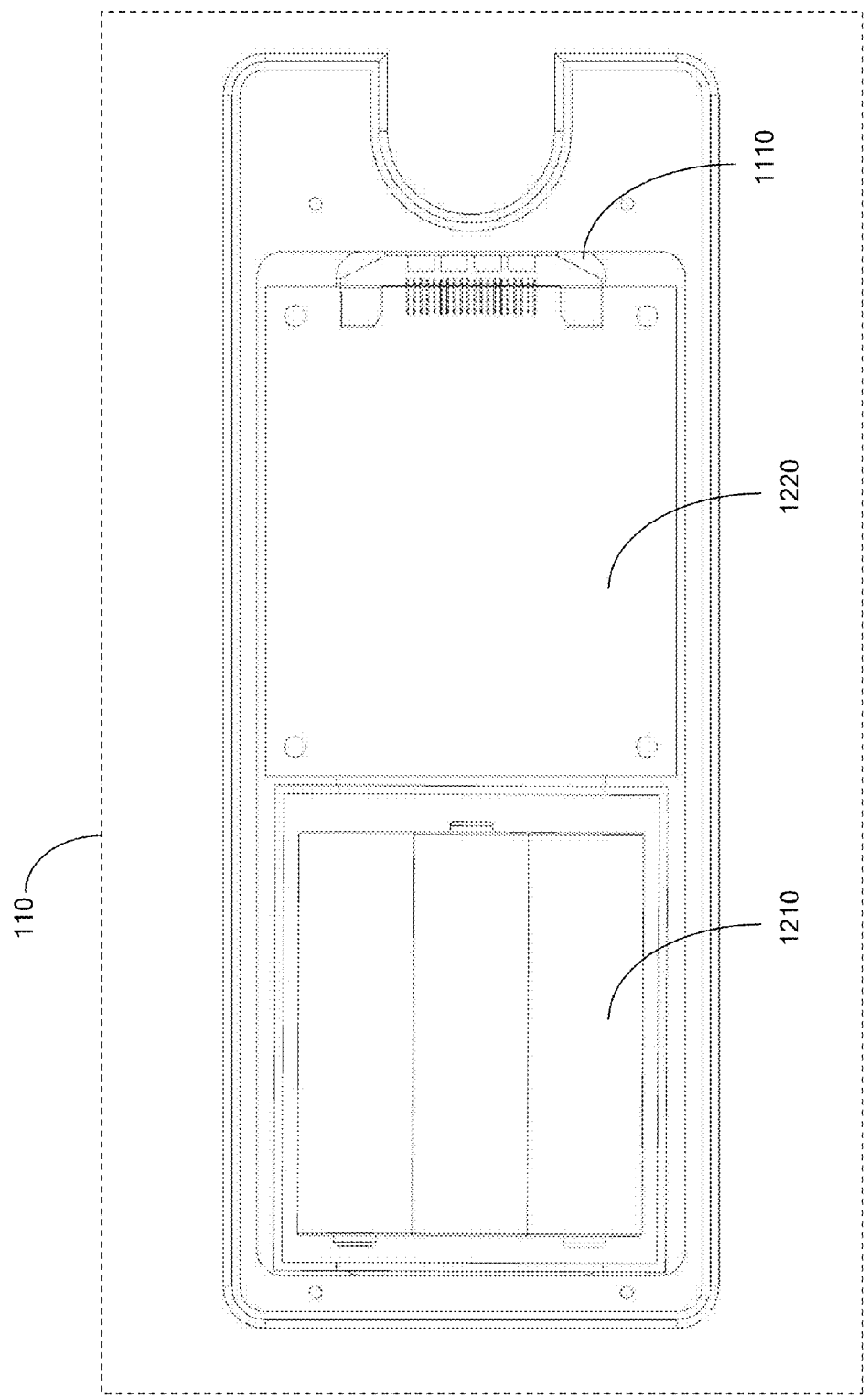
FIG. 12 illustrates a top view of the control device showing the placement of the battery pack and controller card according to an embodiment of the invention.
Figure 13:
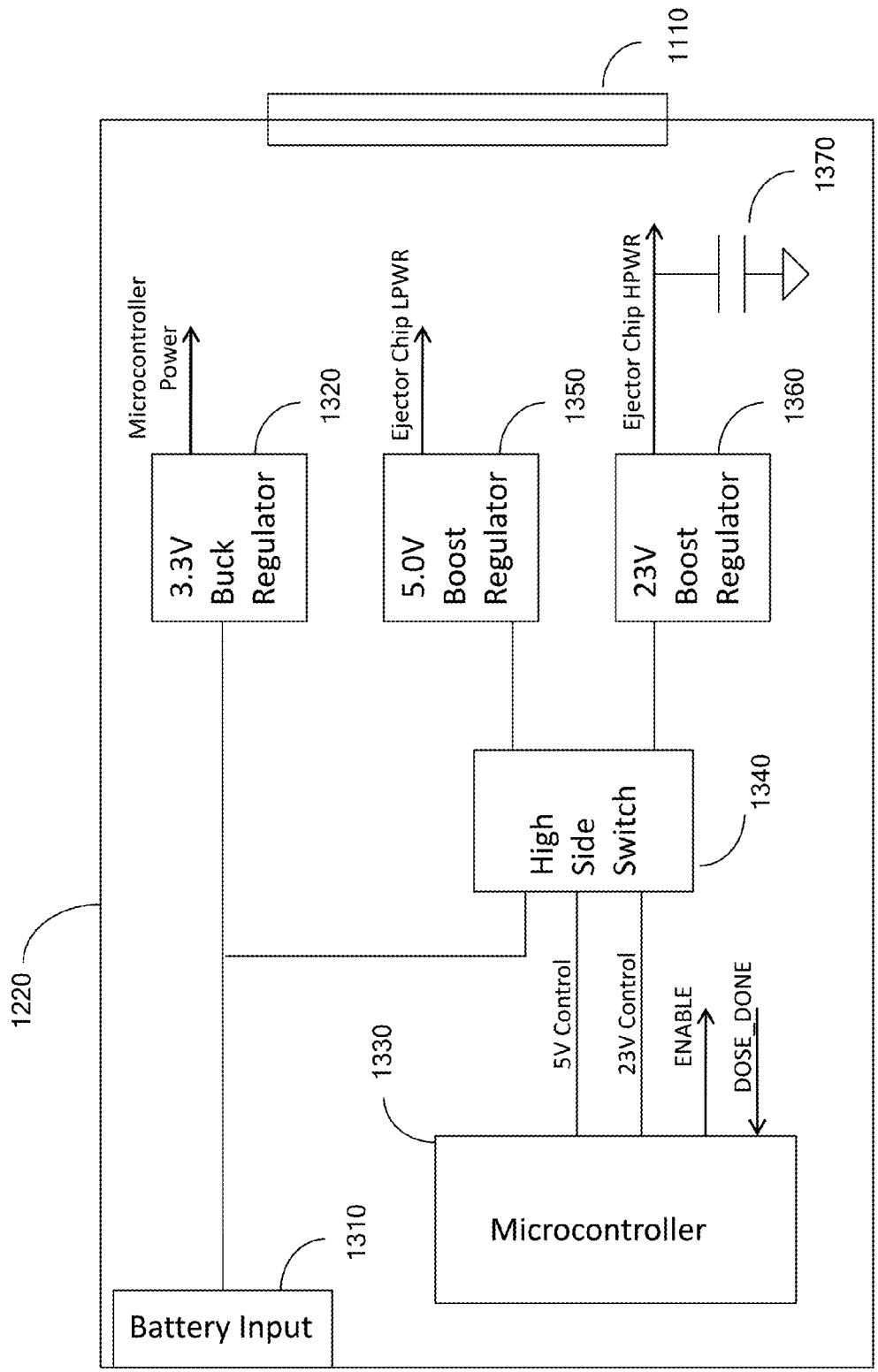
FIG. 13 is a block diagram of the controller card according to an embodiment of the invention.

FIG. 12 shows the interior view of the control device 110. As shown the device contains a battery pack 1210 and controller card 1220 which enables operation of the fluid cartridge 120. An exemplary embodiment of the controller card is shown in FIG. 13 and now described.

Battery Input 1310 accepts a voltage provided by the battery pack 1210. In this application 3 AA batteries are used which provide a nominal voltage of 4.5V. This voltage is passed to a 3.3V Buck Regulator 1320 which converts the input to 3.3V which is used to power the Microcontroller 1330. The Microcontroller provides control signals to a High Side Switch 1340 which is used to gate the battery voltage to a 5.0V Boost Regulator 1350 and a 23V Boost Regulator 1360. In this way the Microcontroller can be used to manage power consumption and prolong battery life. When enabled the 5.0V Boost Regulator will provide logic power (LPWR) voltage to the ejector chip 130. When the 23V Boost Regulator is enabled it provides the voltage required to drive resistive elements on the ejector chip used for thermal drop generation (HPWR). The Microcontroller can also be programmed to provide the desired power up/down sequence for the ejector chip. In the case of the power down sequence it is usually desirable to allow a method to discharge charge storage capacitor 1170 on the controller card. In the exemplary embodiment the 23V Boost Regulator is switched off by the Microcontroller but the 5.0V Boost Regulator is left on. In this way Temperature Sensor/Control Circuit 260 will continue to operate and thus provides a path to discharge the capacitors. In this embodiment the Microcontroller is also used to provide and logic enable signal (ENABLE) to the ejector chip. In this instance the ENABLE signal is raised in response to the Microcontroller receiving an input from a touch sensor (not shown) incorporated into the top of the control device 110. The Microcontroller also receives the DOSE_DONE flag sent from the ejector chip. This provides confirmation to the control device that the proper dose has been delivered and can be used to begin the proper power down sequence.

While this embodiment uses a microcontroller to add logic functions to the controller is should be apparent that the design of the ejector chip 130 is such that a microcontroller is not required. Those skilled in the art will recognize that analog circuits can be configured to provide the properly sequenced LPWR, HPWR and ENABLE signals. It should also be apparent that the controller card 1220 would not be limited to battery operation only.

The liquid dispense system as described will have broad applications in fields requiring controlled liquid dispensing such as POC diagnostic, lab automation or drug delivery. For example in a handheld POC device designed to measure acetone levels in a users breath it may be necessary to first hydrate a sensor strip before making an impedance measurement of the strip. The fluid dispense system described by this invention would simplify the addition of the hydration means since the interface to the handheld device is minimal. In the case of lab automation applications, complete fluid cartridges with or without bottles, could be purchased with pre-programmed dispense volumes. These could then be used coupled with a control device forming an accurate method for dispensing small volumes of liquid. The system would also find use in drug delivery where it is desirable to deliver a controlled dose to the patient. In this case the system would provide a tamper resistant delivery system by filling and programming the fluid cartridge at manufacturing.

The invention claimed is:

1. A handheld fluid cartridge to hold a volume of fluid for dispensing and for docking with a control device, comprising:

a bottle to retain the volume of fluid;

an ejector chip on a board in fluid communication with the bottle to receive the volume of fluid and having pluralities of ejectors that cause ejection of the fluid upon actuation, wherein the bottle defines a fixed volume selected from a plurality of bottles modularly attachable to the ejector chip by way of a substrate attached to the board and having ribs for user manipulation; and control logic in electrical communication with the ejector chip and programmed to cause said actuation of the ejectors, wherein the control logic includes a memory that stores an energy pulse profile, a pre-specified amount of the volume of fluid to be ejected by the ejectors during use, and a desired temperature at which the pre-specified amount of the volume of fluid is to be ejected, a fire signal generator in communication with the memory and programmed to supply electrical signals to the ejectors according to the energy pulse profile for ejecting the pre-specified amount of the volume of fluid from the ejector chip, a dose control logic circuit in communication with the memory and that is programmed to prevents further ejection of the volume of fluid upon reaching said pre-specified amount, the dose control logic circuit including an output signal that confirms to the control device when docked that a proper dose of fluid has been ejected or not from the bottle, and a temperature control circuit in communication with the memory that inhibits ejection of any of the volume of fluid until a temperature of the fluid to be ejected is within a predefined acceptable range of the desired temperature.

2. The fluid cartridge of claim 1, wherein the fixed volume ranges from about 0.5 mL to about 5 mL.

3. The fluid cartridge of claim 1, wherein the pre-specified amount of the volume of fluid is within a range of about 24 pL to about 402 uL.

4. The fluid cartridge of claim 1, wherein the predefined acceptable range of the temperature of the fluid to be ejected is within three degrees Celsius of the desired temperature stored in the memory.

5. The fluid cartridge of claim 1, wherein the control logic further includes address control logic that only addresses the ejectors in ejector groups (G) having a given number of individual ejectors (H).

6. The fluid cartridge of claim 5, wherein G×H is 16×16.

7. The fluid cartridge of claim 1, wherein a physical spacing of the ejectors on the ejector chip defines a maximum dispense area for the volume of fluid.

8. The fluid cartridge of claim 7, wherein the ejectors (H) number two hundred fifty-six total ejectors (H1-H256) and are arranged in four columns each having sixty-four ejectors such that the columns define the total ejectors (H1-H256) in column 1 as (H1-H64), column 2 as (H65-H128), column 3 as (H129-H192) and column 4 as (H193-H256).

9. The fluid cartridge of claim 8, wherein a first distance in a vertical direction of the ejector chip between ejectors H1 and H64 is about 4 mm and a second distance in a horizontal direction of the ejector chip between ejectors H1 and H193 is about 2 mm.

10. The fluid cartridge of claim 7, wherein the maximum dispense area corresponds to a distance of sixteen adjacent said ejectors.

11. The fluid cartridge of claim 7, wherein the maximum dispense area is about 8 mm.

12. The fluid cartridge of claim 1, wherein the memory further stores a spatial pattern of the ejectors that delimits a dispense area on the ejection chip from which the pre-specified amount of the volume of fluid can be ejected during use.

13. The fluid cartridge of claim 1, further including an address control logic in communication with the memory that generates address information for addressing one or more of the ejectors according to the spatial pattern of the ejectors.

14. A handheld fluid cartridge to hold a volume of fluid for dispensing and for docking with a control device, comprising:
a bottle to retain the volume of fluid;
a substrate connected to the bottle having ribs for user manipulation;
an ejector chip on a board in fluid communication with the bottle to receive the volume of fluid and having pluralities of ejectors that cause ejection of the fluid upon actuation, the ejector chip connecting to the substrate by way of the board; and
control logic in electrical communication with the ejector chip to cause said actuation of the ejectors, wherein the control logic includes
a memory in the form of polysilicon fuses that stores a spatial pattern of the ejectors as arranged on the ejector chip that delimits a dispense area on the ejection chip from which the pre-specified amount of the volume of fluid can be ejected during use, and
an address control logic in communication with the memory that is programmed to generates address information for addressing one or more of the ejectors according to the spatial pattern of the ejectors.

15. A handheld fluid cartridge system for dispensing a volume of fluid, comprising:
a control device having
a handheld housing,
a power source mounted with the housing, and a connector port having first electrical contacts; and a fluid cartridge for docking externally to the handheld housing of the control device for ease in separation of the control device from the fluid cartridge so other fluid cartridges can be docked externally thereto, the fluid cartridge having a board for releasably mating with the connector port of the control device, the board having second electrical contacts for contacting the first
electrical contacts during mating for receiving electrical power from the power source of the control device,
a bottle to retain the volume of fluid, a substrate connected to the bottle having ribs for user manipulation to allow the user to push or pull the bottle and substrate nearer or farther from the connector port, thereby connecting or not the electrical contacts of the board,
an ejector chip connected to the board residing in electrical communication with the second electrical contacts and fluid communication with the bottle to receive the volume of fluid, the ejector chip having pluralities of ejectors that cause ejection of the fluid upon actuation, wherein the bottle defines a fixed volume selected from a plurality of bottles modularly attachable
to the ejector chip by way of the substrate, and
control logic in electrical communication with the ejector chip and programmed to cause said actuation of the ejectors, wherein the control logic includes
a memory that stores an energy pulse profile, a pre-specified amount of the volume of fluid to be ejected by the ejectors during use, and a desired temperature at which the pre-specified amount of the volume of fluid is to be ejected,
a fire signal generator in communication with the memory and programmed to supply electrical signals to the ejectors according to the energy pulse profile for ejecting the pre-specified amount of the volume of fluid from the ejector chip,
a dose control logic circuit in communication with the memory and that is programmed to prevents further ejection of the volume of fluid upon reaching said pre-specified amount, the dose control logic circuit including an output signal that confirms to the control device when docked that a proper dose of fluid has been ejected or not from the bottle, and
a temperature control circuit in communication with the memory that inhibits ejection of any of the volume of fluid until a temperature of the fluid to be ejected is within a predefined acceptable range of the desired temperature.

16. The handheld fluid cartridge system of claim 15, wherein the memory stores a spatial pattern of the ejectors as arranged on the ejector chip that delimits a dispense area on the ejection chip from which the pre-specified amount of the volume of fluid can be ejected during use.

17. The handheld fluid cartridge system of claim 16, wherein the control logic further include an address control logic in communication with the memory that generates address information for addressing one or more of the ejectors according to the spatial pattern of the ejectors.

18. The handheld fluid cartridge system of claim 16, wherein the board is a printed circuit board and the connector port is an edge card connector.

* * * * *